United States Patent
Modine

(10) Patent No.: US 10,925,725 B2
(45) Date of Patent: Feb. 23, 2021

(54) PROSTHETIC MITRAL OR TRICUSPID HEART VALVE

(71) Applicant: Thomas Modine, La Madeleine (FR)

(72) Inventor: Thomas Modine, La Madeleine (FR)

(73) Assignee: VALMY HOLDINGS, Villeneuve (FR)

( * ) Notice: Subject to any disclaimer, the term of this patent is extended or adjusted under 35 U.S.C. 154(b) by 191 days.

(21) Appl. No.: 15/311,213

(22) PCT Filed: Jan. 22, 2015

(86) PCT No.: PCT/IB2015/050498
§ 371 (c)(1),
(2) Date: Dec. 26, 2016

(87) PCT Pub. No.: WO2015/177655
PCT Pub. Date: Nov. 26, 2015

(65) Prior Publication Data
US 2017/0100241 A1    Apr. 13, 2017

(30) Foreign Application Priority Data
May 23, 2014  (FR) ...................................... 1454678

(51) Int. Cl.
*A61F 2/24*     (2006.01)
*A61F 2/848*    (2013.01)

(52) U.S. Cl.
CPC .......... *A61F 2/2418* (2013.01); *A61F 2/2412* (2013.01); *A61F 2/848* (2013.01);
(Continued)

(58) Field of Classification Search
CPC ........ A61F 2/24; A61F 2/2412; A61F 2/2418; A61F 2220/0008; A61F 2220/0016;
(Continued)

(56) References Cited

U.S. PATENT DOCUMENTS 10,478,290 B2 * 11/2019 Emani .................... A61F 2/2409
10,722,352 B2 *  7/2020 Spence ..................... A61F 2/24
(Continued)

FOREIGN PATENT DOCUMENTS

| JP | 2013-523218 | 6/2013 |
|---|---|---|
| WO | 2009/132187 | 10/2009 |

(Continued)

*Primary Examiner* — Seema Mathew
(74) *Attorney, Agent, or Firm* — Law Offices Of Steven W. Weinrieb

(57) ABSTRACT

This prosthesis (1), comprises an expandable tubular frame (2) with a mesh structure and a prosthetic valve (3) mounted on this frame;
 the ventricular portion (2v) of the frame (2) has a large indentation (6) on one side, extending lengthwise from the end of this ventricular portion (2v) that is opposite said annular portion (2i) to the part of this ventricular portion (2v) close to the annular portion (2i), this indentation (6) extending over a sector of the circumference of the prosthesis (1) of about 90 to 140°;
 said atrial portion (2a) flares toward the outside of the prosthesis, from said annular portion (2i) toward the end of this atrial portion opposite this annular portion, and comprises anchoring spikes (5a) on the side of said annular portion (2i); and
 said ventricular portion (2v) has a substantially spherical or ovoid shape and comprises anchoring spikes (5v) on the side of said annular portion (2i).

1 Claim, 3 Drawing Sheets

(52) U.S. Cl.
CPC ............... *A61F 2002/8483* (2013.01); *A61F 2230/0071* (2013.01); *A61F 2230/0076* (2013.01); *A61F 2230/0078* (2013.01)

(58) Field of Classification Search
CPC ............ A61F 2250/0039; A61F 2/856; A61F 2002/8483; A61F 2/848; A61F 2002/8486
See application file for complete search history.

(56) References Cited

U.S. PATENT DOCUMENTS

| | | | | |
|---|---|---|---|---|
| 2004/0054403 A1* | 3/2004 | Israel | ................... | A61F 2/915 623/1.35 |
| 2007/0167980 A1* | 7/2007 | Figulla | ............... | A61B 17/0057 606/213 |
| 2007/0233229 A1* | 10/2007 | Berra | .................. | A61F 2/07 623/1.13 |
| 2012/0215303 A1* | 8/2012 | Quadri | ................ | A61F 2/2427 623/2.18 |
| 2014/0052237 A1* | 2/2014 | Lane | .................... | A61F 2/2418 623/2.11 |
| 2014/0135908 A1 | 5/2014 | Glozman et al. | | |
| 2014/0214157 A1* | 7/2014 | Bortlein | ............... | A61F 2/2418 623/2.11 |
| 2014/0288480 A1* | 9/2014 | Zimmerman | ............. | A61F 2/89 604/8 |
| 2014/0358223 A1* | 12/2014 | Rafiee | ................... | A61F 2/2418 623/2.13 |
| 2015/0088248 A1* | 3/2015 | Scorsin | ................ | A61F 2/2418 623/2.11 |
| 2015/0196390 A1* | 7/2015 | Ma | ....................... | A61F 2/2418 623/2.17 |
| 2016/0067067 A1* | 3/2016 | Roselli | ................... | A61F 2/856 623/1.16 |
| 2016/0120643 A1* | 5/2016 | Kupumbati | ........... | A61F 2/2418 623/2.18 |
| 2017/0007392 A1* | 1/2017 | Louren O | ............... | A61F 2/856 |
| 2017/0014228 A1* | 1/2017 | Emani | .................. | A61F 2/2418 |
| 2017/0266003 A1* | 9/2017 | Hammer | ............... | A61F 2/2418 |
| 2017/0360558 A1* | 12/2017 | Ma | ....................... | A61F 2/2409 |
| 2018/0271651 A1* | 9/2018 | Christianson | ......... | A61F 2/2418 |
| 2018/0303612 A1* | 10/2018 | Pasquino | ............. | A61F 2/2448 |
| 2018/0325662 A1* | 11/2018 | Modine | ................ | A61F 2/2487 |

FOREIGN PATENT DOCUMENTS

| | | | | |
|---|---|---|---|---|
| WO | 2013/037519 | | 3/2013 | |
| WO | WO-2013160439 A1 | * | 10/2013 | ........... A61F 2/2412 |

* cited by examiner

PROSTHETIC MITRAL OR TRICUSPID HEART VALVE

BACKGROUND OF THE INVENTION

A well-known pathology of a heart valve, primarily affecting elderly patients, is the distention of the valve annulus, this distention leading to poor coaptation of the valves and therefore loss of sealing and effectiveness of the valve.

It is known to treat this pathology by annuloplasty, i.e., by placing a total or partial prosthetic annulus aiming to recalibrate the native valve annulus. This technique has certain drawbacks, in particular that of not being very suitable for elderly patients.

It is also known to implant, above the native valve, a prosthesis comprising an expandable tubular frame and a prosthetic valve mounted on this frame. The tubular frame, frequently called "stent", has a mesh structure, and comprises an atrial portion, i.e., intended to be placed at the atrium of a heart, a ventricular portion, i.e., intended to be placed at the ventricle of a heart, and, an annular portion, i.e., intended to be placed at the native valve annulus, situated between these atrial and ventricular portions. The frame may be self-expandable (in particular being made from a shape memory material) or made from an expandable material using a balloon. The prosthetic valve may in turn be made from a synthetic or natural material.

Such a prosthesis is deformable so as to be able to placed in a catheter and is intended to be deployed from this catheter at the native valve to be treated. It may be placed using the apical approach (i.e., from the lower tip of the heart) or using a transseptal (mitral valve) or jugular or femoral (tricuspid valve) approach.

The existing prostheses of this type are not fully satisfactory, in particular having a risk of bothering, when they are placed, the operation of the aortic valve and risks of migration and therefore obstruction of the ventricular ejection path. Furthermore, these prostheses are not always very easy to place, and their shape is not perfectly adapted to that of the implantation site.

OBJECTS OF THE INVENTION

The present invention aims to resolve these essential drawbacks.

SUMMARY OF THE INVENTION

The prosthesis comprises an expandable tubular frame with a mesh structure and a prosthetic valve mounted on the frame, said frame comprising an atrial portion, a ventricular portion and an annular portion situated between these atrial and ventricular portions;
- said ventricular portion has a large indentation on one side, extending lengthwise from the end of this ventricular portion that is opposite said annular portion to the part of this ventricular portion close to the annular portion, this indentation extending over a sector of the circumference of the prosthesis of about 90 to 140°;
- said atrial portion flares toward the outside of the prosthesis, from said annular portion toward the end of this atrial portion opposite this annular portion, and comprises, on the side of said annular portion, on at least part of its circumference, anchoring spikes protruding from its outer face; and
- said ventricular portion has a substantially spherical or ovoid shape and comprises, on the side of said annular portion, on at least part of its circumference, anchoring spikes protruding from its outer face.

The indentation thus interrupts the mesh structure of the frame and imparts an asymmetrical shape to the ventricular portion of the prosthesis; this indentation is intended to be turned toward the wall of the ventricle situated near the aortic valve, this zone being called "mitral and aortic continuity" or "tricuspido-aortic". It allows an absence of mesh structure across from this wall and therefore allows the prosthesis to have no risk of excessive bearing against the wall of the ventricle to the right of the aortic valve, which may hinder the operation of this aortic valve.

The inventor has, however, foreseen that reducing the bearing surface of the prosthesis against the wall of the ventricle, due to the indentation, was greatly increasing the risk of migration of the prosthesis and therefore of obstruction of the ventricular ejection path; the inventor was therefore able to conceive that the adoption of such an indentation involved ensuring complete anchoring of the prosthesis at the implantation site, and that it was necessary, to that end, to arrange anchoring spikes on said atrial portion and on said ventricular portion, in locations close to said annular portion, able to be inserted in the depth of the annulus of the treated valve.

When the prosthesis is placed using the apical approach, its atrial portion is first deployed and brought against the atrial part of the valve annulus; the flared shape of this atrial portion is well suited to wide bearing against this atrial part of the annulus; once said atrial portion is deployed, the different anchoring spikes comprised by this atrial portion are able to be inserted into said atrial part of the annulus when the catheter is removed in order to free the other portions of the frame. Good pre-positioning of the prosthesis with respect to the implantation site is thus ensured. The continued withdrawal of the catheter causes the gradual deployment of the ventricular portion; in light of the spherical or ovoid shape of this ventricular portion, this deployment produces a radial expansion of the wall of this ventricular portion, which leads the different anchoring spikes comprised by this ventricular portion to be inserted into the ventricular part of the valve annulus, from the beginning of the deployment, thus causing perfect locking of the prosthesis on the native valve annulus. This locking is even more efficient when the spherical or ovoid shape of the ventricular portion allows a close application of the frame against said ventricular part of the valve annulus.

This same spherical or ovoid shape allows bearing of the frame that is well-suited to the shape of the ventricle near the valve annulus and that does not conflict with the underlying anatomical structures.

The prosthesis thus structured makes it possible to perfectly achieve the aforementioned aim of obtaining a prosthesis that, when in place, does not hinder the operation of the aortic valve while having very low migration risks and being relatively easy to place and having a shape well-suited to that of the implantation site.

It should be noted that the prosthesis according to the invention may be implanted using a transseptal (mitral valve) or jugular or femoral (tricuspid valve) approach, in which case the ventricular portion is deployed first and the atrial portion is deployed second, with insertions of anchoring spikes of the ventricular portion, then of the atrial portion, in the annulus, which are done similarly to the manner described above.

Preferably, said indentation extends over a sector of the circumference of the prosthesis of about 120°.

Preferably, said anchoring spikes are in the form of curved claws developing toward the outside of the prosthesis from their bases toward their pointed free ends.

The anchoring spikes thus configured produce effective anchoring.

The anchoring spikes are preferably present on the entire circumference of the prosthesis; they are preferably regularly distributed on this circumference.

According to a first possibility, the anchoring spikes comprised by said atrial portion are situated across from, i.e. opposite, the anchoring spikes comprised by said ventricular portion in the longitudinal direction of the prosthesis.

The anchoring is thus done by clamp effect done by the different pairs of anchoring spikes, which allows very effective anchoring. The particularity of these spikes is then forming a sort of "crab claw" due to the fact that the points are oriented symmetrically toward one another, making it possible to bite the annular tissue and stabilize the frame of the valve. During the deployment of the prosthesis with the use of the apical approach, the atrial anchoring spikes deploy first, making it possible to catch the annular tissue, then, secondly, over the course of the deployment, the ventricular anchoring spikes deploy in turn and make it possible to perfect the anchoring of the prosthesis, with maintenance of the anchoring spikes in the intra-annular position.

Thus, the proposed structure allows an implantation that bears on the peri-annular valve tissue first (the anchoring spikes), which is followed by additional bearing on the valve annulus. Indeed, the claw catching system allows catching of the valve tissue and is completed by the intra-annular bearing of the metal structure, in the mitral and tricuspid position as required by the approach used.

The prosthesis may in particular comprise six pairs of atrial anchoring spikes and ventricular anchoring spikes.

According to a second possibility, in the deployed state of the prosthesis:

each anchoring spike has a substantially rectilinear base portion, protruding from the portion of the prosthesis in a direction forming an angle from 35 to 55° relative to the longitudinal axis of the prosthesis, and a free end portion that is bent relative to said base portion and oriented along a substantially circumferential direction of the prosthesis;

the free end portion of an atrial anchoring spike is oriented toward the free end portion of an adjacent ventricular anchoring spike, close in the circumferential direction but angularly offset relative to this atrial anchoring spike; reciprocally, the free end portion of a ventricular anchoring spike is oriented toward the free end portion of an adjacent atrial anchoring spike, close in the circumferential direction but angularly offset relative to this ventricular anchoring spike.

This form of the anchoring spikes allows effective anchoring of the prosthesis to the annulus of the treated valve.

It will be understood that the expression "atrial anchoring spike" refers to an anchoring spike present on said atrial portion, and the expression "ventricular anchoring spike" refers to an anchoring spike present on said ventricular portion.

Preferably, each base portion protrudes along a direction forming an angle of about 45° relative to the longitudinal axis of the prosthesis.

Preferably, on each spike, the length of the base portion is about two to three times that of the free end portion.

Preferably, for a prosthesis to treat a mitral valve, the anchoring spikes are distributed as follows on the circumference of the frame of the prosthesis: one spike situated on the zone of this frame found at the anterior trigone after implantation, one spike situated on the zone of the frame found at the posterior trigone after implantation, one spike situated on the zone of the frame found at the anterior commissure of the mitral valve after implantation, one spike situated on the zone of the frame found at the posterior commissure of the mitral valve after implantation, one spike situated on the zone of the frame found at the middle of the posterior annulus of the mitral valve after implantation, and one spike situated on the zone of the frame found at the middle of the anterior annulus of the mitral valve after implantation.

Preferably, the mesh structure of the frame comprises, at said atrial and annular portions, and at the ventricular portion comprising said anchoring spikes, diamond-shaped meshes connected to one another by their corners. When the anchoring spikes are according to the aforementioned first possibility, they may have their bases connected to the portions of the meshes that form at the opposite corners of these meshes in the atrial-ventricular direction of the prosthesis, these anchoring spikes protruding from these portions of the meshes.

This mesh structure allows the frame to bear effectively against the corresponding parts of the valve annulus and to ensure proper insertion of said anchoring spikes into this annulus.

Preferably, the mesh structure of the frame comprises, at the part of the ventricular portion with no anchoring spikes, teardrop-shaped mesh frames, with two adjacent meshes arranged head to tail relative to one another.

This mesh structure allows the frame to have significant flexibility at said ventricular portion part, adapted to bearing against the wall of the ventricle of a heart.

Preferably, when the prosthesis is intended to treat a mitral valve, the atrial portion and the annular portion of the prosthesis have a noncircular cross-section, in the shape of a "D with rounded corners and edges".

It will be understood that the expression "cross-section" refers to the section of the prosthesis perpendicular to the longitudinal axis of the prosthesis.

These atrial and annular portions thus have a shape well suited to that of the atrium near the annulus of a mitral valve and this annulus.

Preferably, the atrial portion of the prosthesis includes a tight wall that covers its meshes. This tight wall, in particular made from polyethylene terephthalate, forms a membrane or sleeve that makes it possible to increase the contact surface of this portion and the heart wall in order to decrease paravalvular leakage, i.e., between the prosthesis and the heart wall.

BRIEF DESCRIPTION OF THE DRAWINGS

The invention will be well understood, and other features and advantages thereof will appear, in reference to the appended schematic drawing, which shows, as non-limiting examples, two possible embodiments of the prosthesis in question.

FIG. 2b is a sectional view of the same portion, along an angle perpendicular to the view according to FIG. 2a;

DESCRIPTION OF THE PREFERRED EMBODIMENTS

Figure 1:
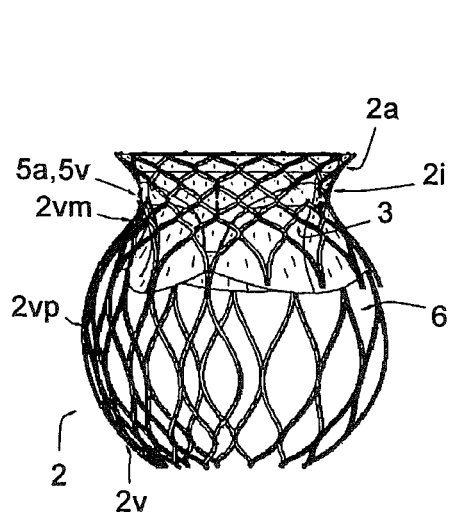
FIG. 1 is a side view according to a first embodiment, with the prosthetic valve comprised by this prosthesis in the open position.
Figure 2A:
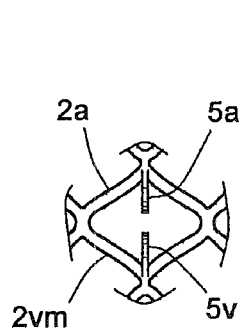
FIG. 2a is an enlarged view of a portion of the prosthesis as shown in FIG. 1, comprising anchoring claws.
Figure 2B:
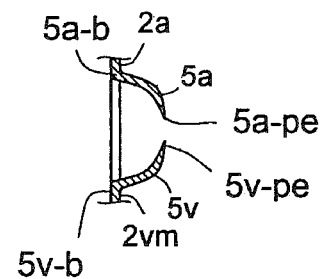
Figure 3:
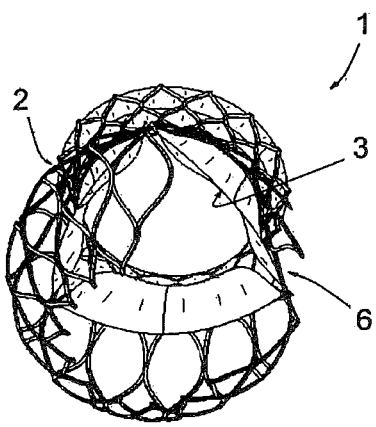
FIG. 3 is a view of the prosthesis by its ventricular end, slightly off-centered, with the prosthetic valve in the open position.
Figure 4:
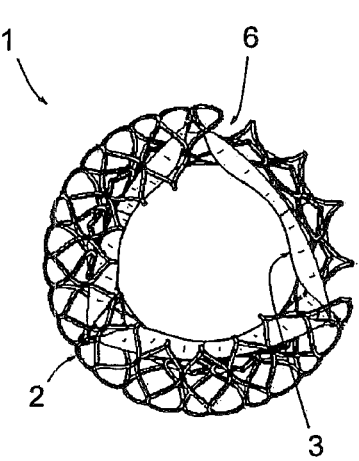
FIG. 4 is a view thereof by its ventricular end, along the axis of this prosthesis, with the prosthetic valve in the open position.
Figure 5:
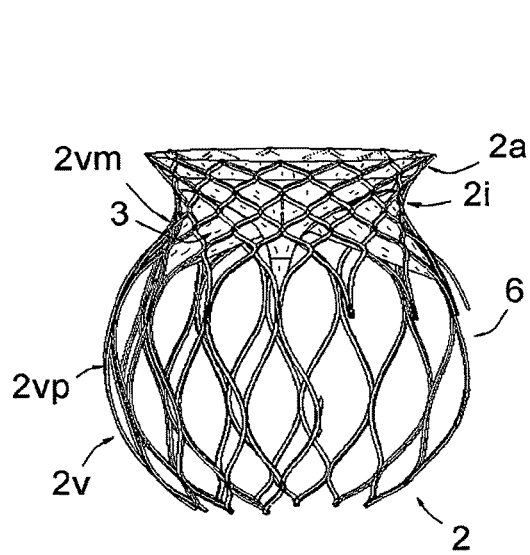
FIG. 5 is a view similar to FIG. 1, with the prosthetic valve in the closed position.
Figure 6:
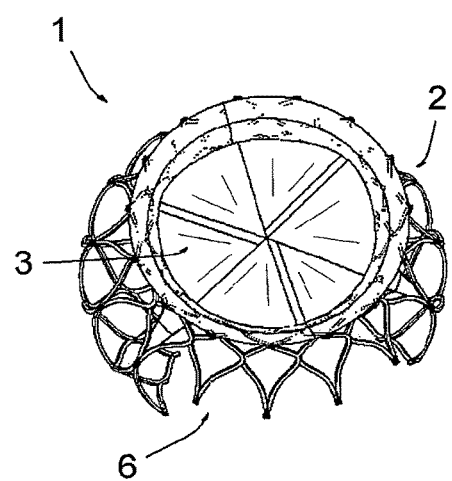
FIG. 6 is a view thereof by its atrial end, slightly off-centered, with the prosthetic valve in the closed position.

FIGS. 1 to 6 show a prosthetic mitral or tricuspid heart valve 1, comprising an expandable tubular frame 2 and a prosthetic valve 3 mounted on this frame.

The frame 2 has a mesh structure made up of elastically deformable filaments, allowing it to assume the deployed form shown in the figures and a contracted form (not shown) in which it can be contained in a catheter for insertion into a heart. The frame 2 may in particular be made, using a known technique, from a shape memory alloy, in particular a nickel and titanium alloy known as Nitinol.

The frame 2 comprises an atrial portion 2a, i.e., intended to be placed at the atrium of a heart, a ventricular portion 2v, i.e., intended to be placed at the ventricle of a heart, and an intermediate annular portion 2i, situated between these atrial 2a and ventricular 2v portions, intended to be placed at the native valve annulus.

In the illustrated deployed state, the atrial portion 2a has a conical shape, the section of which increases from the annular portion 2i, and having an apical angle of about 120°. It is formed by diamond-shaped meshes connected to one another by their corners, and comprises six anchoring claws 5a regularly distributed on its circumference. As more particularly shown in FIGS. 2a and 2b, the bases 5a-b of these claws 5a are connected to the mesh portions that form the corners of the meshes situated on the atrial side of the prosthesis 1, and protrude from these portions of the meshes toward the ventricular side of the prosthesis. These claws 5a are curved and develop toward the outside of the prosthesis from these bases 5a-b toward their pointed free end portions 5a-pe.

The intermediate annular portion 2i is formed by the same diamond-shaped meshes as the atrial portion 2a, in the continuation of these meshes.

The ventricular portion 2v has a substantially ovoid shape. It comprises a marginal part 2vm close to the intermediate annular portion 2i, connected to the latter, including anchoring claws 5v, and a primary part 2vp connected to this marginal part on the side opposite the portion 2i, having a wide indentation 6.

The marginal part 2vm is formed by the same diamond-shaped meshes as the atrial portion 2a and the intermediate portion 2i, in the continuation of these meshes. The claws 5v that it comprises are situated across from, or opposite to, the atrial claws 5a, as can clearly be seen in FIG. 2a, have a structure identical to that of the atrial claws 5a, have their bases 5v-b connected to the portions of the meshes that form the corners of the meshes situated on the ventricular side of the prosthesis 1, protrude from these portions of the meshes, and are curved and develop toward the outside of the prosthesis 1 from the bases 5v-b toward their pointed free end portions 5v-pe.

The primary part 2vp is formed by teardrop-shaped meshes, arranged head to tail from one mesh to an adjacent mesh.

The indentation 6 extends lengthwise from the end of the ventricular portion 2v opposite the annular portion 2i to its marginal part 2vm, and extends over a sector of about 120°. It thus imparts an asymmetrical shape to the ventricular portion 2v.

The prosthetic valve 2 is of a known type, made from a synthetic or natural material (such as pig pericardium). In the illustrated example, it comprises three valves.

In practice, the prosthesis 1 is contracted and placed in a catheter for insertion into a heart. This catheter comprises radiopaque markers making it possible to view the angular orientation of this catheter, and therefore the prosthesis 1, in order to orient the prosthesis angularly before deploying it.

The catheter may be inserted into a heart through the apical approach and is oriented angularly so as to orient the prosthesis 1 such that the indentation 6 is turned toward the wall of the ventricle housing the aortic valve, this zone being called mitral and aortic continuity.

The atrial portion 2a of the prosthesis 1 is first deployed and brought against the atrial part of the valve annulus; the conical shape of this atrial portion is well suited to wide bearing against this atrial part of the annulus; once said atrial portion is deployed, the different anchoring spikes 5a are oriented to be inserted into said atrial part of the annulus when the catheter is removed in order to free the other portions of the frame 2. Good pre-positioning of the prosthesis 1 with respect to the implantation site is thus ensured.

The continued withdrawal of the catheter causes the gradual deployment of the ventricular portion 2v; in light of the ovoid shape of this ventricular portion, this deployment produces a radial expansion of the wall of this ventricular portion 2v, which leads the different anchoring spikes 5v to be inserted into the ventricular part of the valve annulus, from the beginning of the deployment, thus causing perfect locking of the prosthesis 1 on the native valve annulus. This locking is even more efficient when the ovoid shape of the ventricular portion 2v allows a close application of the frame 2 against said ventricular part of the valve annulus.

This same ovoid shape allows bearing of the frame 2 that is well-suited to the shape of the ventricle and that does not conflict with the underlying anatomical structures.

The indentation 6 interrupts the mesh structure of the frame 2 and makes it possible for the prosthesis according to the invention not to present any risk of hindering the proper operation of the aortic valve or obstructing the ventricular flush chamber.

It should be noted that the prosthesis according to the invention could be implanted using a transseptal (mitral valve) or jugular (tricuspid valve) approach, in which case the ventricular portion 2v is deployed first and the atrial portion 2a is deployed second, with insertions of anchoring spikes 5v, 5a of the ventricular portion, then of the atrial portion, in the annulus, which are done similarly to the manner described above.

Figure 7:
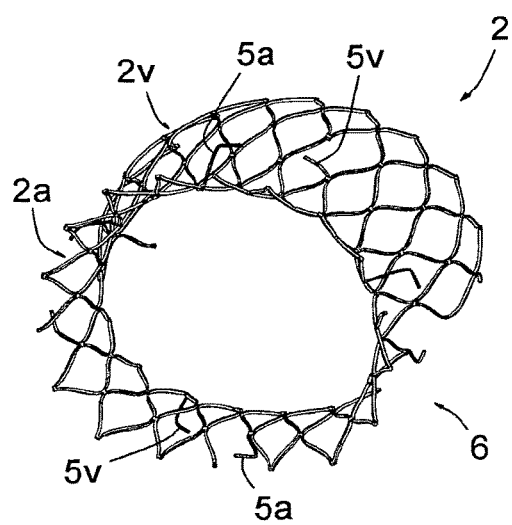
FIG. 7 is a perspective view of the frame comprised by the prosthesis according to a second embodiment.
Figure 8:
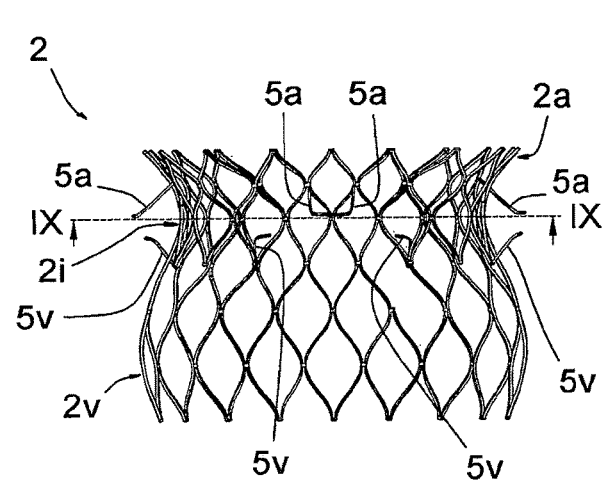
FIG. 8 is a side view thereof.
Figures 9, 10:
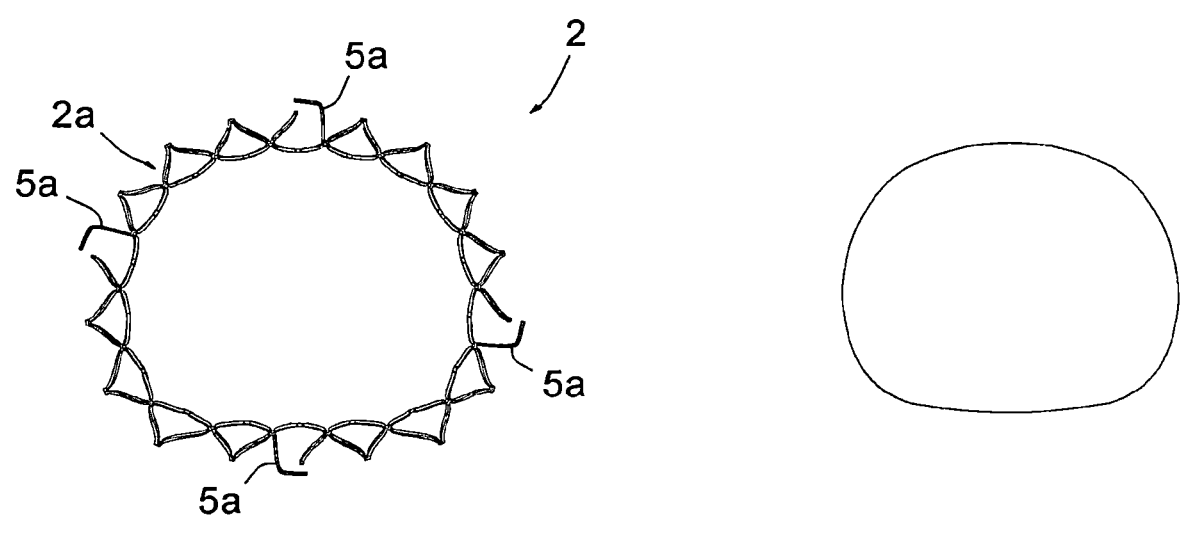
FIG. 9 is a sectional view thereof along line IX-IX of FIG. 8.
FIG. 10 is a view of the shape of the conduit defined by the annular portion of the prosthesis, as shown in FIG. 9.

FIGS. 7 to 9 show, from different angles, a second embodiment of the frame 2 of the prosthesis (the prosthetic valve is not shown), intended to treat a mitral valve. For simplification, the parts or elements already described, that are found in this 2nd embodiment, are designated using the same numerical references.

In this case, the atrial portion 2a is not conical in that it has a cross-section that is not circular, but rather in the shape of a "D with rounded corners and edges" visible in FIG. 9 and shown schematically in FIG. 10. In reference to this FIG. 10, it appears that this section has a rounded posterior portion, a slightly rounded anterior portion and two rounded lateral portions, these different portions being connected to one another by intermediate portions with a smaller curve radius than they themselves have. It will be understood the terms "posterior" and "anterior" above respectively refer to the portion of the prosthesis situated on the posterior side of the mitral valve annulus and on the anterior side of this same annulus after implantation.

In the same manner as on the frame according to the first embodiment, the atrial portion 2a flares toward the outside of the prosthesis, having a section increasing from said annular portion 2i toward the end of this atrial portion 2a opposite this annular portion 2i.

The annular 2i and ventricular 2v portions have shapes similar to those of the prosthesis according to the first embodiment, except that the ventricular portion 2v is closed less at its end opposite the annular portion 2i, being truncated relative to that according to the first embodiment.

The frame 2 according to the second embodiment differs from those according to the first embodiment by the shape of the anchoring spikes 5a, 5v. Indeed, each anchoring spike 5a, 5v has a base portion connected to the corresponding portion 2a, 2v of the frame 2 and a free end portion that is bent relative to said base portion. This base portion is substantially rectilinear and protrudes from the portion 2a, 2v in a direction forming an angle of about 45° relative to the longitudinal axis of the frame (see in particular FIG. 8); it has a length of about two to three times that of the free end portion. The latter is bent relative to the base portion and oriented in a substantially circumferential direction of the prosthesis.

It appears that the anchoring spikes 5a, 5v are distributed as follows on the circumference of the frame 2: one spike situated on the zone of this frame found at the anterior trigone after implantation, one spike situated on the zone of the frame 2 found at the posterior trigone after implantation, one spike situated on the zone of the frame 2 found at the anterior commissure of the mitral valve after implantation, one spike situated on the zone of the frame 2 found at the posterior commissure of the mitral valve after implantation, one spike situated on the zone of the frame 2 found at the middle of the posterior annulus of the mitral valve after implantation, and one spike situated on the zone of the frame 2 found at the middle of the anterior annulus of the mitral valve after implantation.

It also appears that the free end portion of an atrial anchoring spike 5a is oriented toward the free end portion of an adjacent ventricular anchoring spike 5v, close in the circumferential direction but angularly offset relative to this atrial anchoring spike 5a; reciprocally, the free end portion of a ventricular anchoring spike 5v is oriented toward the free end portion of an adjacent atrial anchoring spike 5a, close in the circumferential direction but angularly offset relative to this ventricular anchoring spike.

In particular considering FIG. 8, it must be understood that, in this side view, the anterior portion of the prosthesis (i.e., that closest to the viewer) is seen superimposed on the posterior portion of the prosthesis, such that the two central atrial points 5a appear close to one another in this FIG. 8 whereas they are situated one on the anterior side of the prosthesis and the other on the posterior side of this prosthesis; the same is true for the two central ventricular points 5v, that situated furthest to the left in this FIG. 8 being associated with the central atrial spike 5a situated furthest to the right, and the atrial spike 5a situated furthest to the left being associated with the ventricular spike 5v situated furthest to the right.

The invention thus provides a prosthetic mitral or tricuspid heart valve 1 having, relative to its counterpart prostheses of the prior art, the decisive advantages of not, when it is placed, bothering the operation of the aortic valve and having a low migration risk, and therefore a low risk of obstructing the ventricular ejection path. Furthermore, this prosthesis is relatively easy to place, and has a shape perfectly adapted to that of the implantation site.

The invention has been described above in reference to embodiments provided as examples. It is of course not limited to these embodiments, but extends to all other embodiments covered by the appended claims.

What is claimed is:

1. A mitral or tricuspid heart valve prosthesis for use in connection with a heart having an aortic valve operatively associated therewith and having a valve annulus, comprising:

an expandable tubular frame defined around a longitudinal axis and comprising a mesh structure and a prosthetic valve mounted upon said frame;

wherein said expandable tubular frame further comprises an atrial portion to be placed at the atrium of a heart, a ventricular portion to be placed at the ventricle of a heart, and an intermediate annular portion interposed between said atrial and ventricular portions intended to be placed at the valve annulus;

wherein said ventricular portion has a substantially circular cross-sectional configuration with a first section, or marginal part, of said ventricular portion that is disposed close to said annular portion, and a second section, or primary part, extending opposite said annular portion from said first section to an end section of said ventricular portion, said first section has a peripheral wall extending around the entire periphery of the first section, said second section has an indentation formed upon one side of said ventricular portion such that said substantially circular cross-sectional configuration is interrupted by said indentation so as not to present any risk of hindering the proper operation of the aortic valve of the heart, wherein said indentation also extends lengthwise from said end section of said ventricular portion, that is disposed opposite said annular portion, to said first section of said ventricular portion that is disposed close to said annular portion, and wherein further, said indentation extends over a circumferential sector of said ventricular portion which subtends an angular extent of approximately 120°;

wherein said atrial portion flares toward the outside of said prosthesis, from said annular portion toward an end of said atrial portion opposite said annular portion, and comprises, upon the side of said annular portion, and upon at least part of its circumference, a first set of arcuately curved, "crab-claw" type anchoring spikes protruding outwardly from an outer face portion of said atrial portion of said prosthesis, each anchoring spike of the first set comprising a base segment connected to said outer face portion of said atrial portion of said prosthesis, a curved portion bent toward said ventricular portion of said prosthesis, and a tapered and sharp free end portion terminating at a pointed free end portion so that said anchoring spikes of said first set of anchoring spikes are configured to be capable of being inserted into an atrial portion of said valve annulus;

wherein said ventricular portion has a substantially spherical shape and comprises, at said first section, upon one side of said annular portion, and upon at least part of its circumference, a second set of arcuately curved, "crab-claw" type anchoring spikes protruding outwardly from an outer face of said first section of said ventricular portion of said prosthesis, each anchoring spike of said second set comprising a base segment connected to said outer face portion of said first section of said ventricular portion of said prosthesis, a curved portion bent toward said atrial portion of said prosthesis, and a tapered and sharp free end portion terminating at a pointed free end portion so that said anchoring spikes of said second set of anchoring spikes are configured to be capable of being inserted into a ventricular portion of said valve annulus;

wherein said respective free end portions of said anchoring spikes of said first and second sets are oriented symmetrically toward one another, making it possible for said first and second sets of spikes to bite into tissue of said valve annulus and thereby achieve a clamping effect;

wherein said free end portions of said first and second sets of arcuately curved anchoring spikes are curved toward each other so as to be disposed adjacent to and disposed directly opposite each other;

wherein said annular portion has a peripheral wall extending around the entire periphery of said annular portion and circumferentially connected to said peripheral wall of said first section;

wherein said anchoring spikes are regularly distributed over the entire circumference of said prosthesis and comprise six pairs of atrial anchoring spikes and six pairs of ventricular anchoring spikes;

wherein said mesh structure of said frame comprises, at said atrial and annular portions, and at said first section of said ventricular portion comprising said anchoring spikes, diamond-shaped meshes connected to one another by their corners;

wherein said anchoring spikes have their bases connected to portions of said mesh structure that form at opposite corners of said portions of said mesh structure within said atrial-ventricular direction of said prosthesis, and wherein said anchoring spikes protrude radially outward from said mesh portions;

wherein said mesh structure of said frame comprises, at said second section of said ventricular portion with no anchoring spikes, teardrop-shaped mesh frames, with two adjacent meshes arranged head to tail relative to one another;

wherein said prosthesis is intended to treat a mitral valve wherein its atrial portion and its annular portion have a noncircular cross-section which has a configuration which is substantially that of a D with rounded corners and edges;

wherein said atrial portion of said prosthesis comprises a tight wall that covers said mesh structure, is fabricated from polyethylene terepthalate, and forms a membrane or sleeve that makes it possible to increase the contact surface of said atrial portion and the heart wall in order to decrease paravalvular leakage, that is, between said prosthesis and the heart wall;

wherein said annular portion interposed between said atrial portion and said ventricular portion is also formed by said diamond-shaped meshes and effectively comprise continuations of said diamond-shaped meshes forming said atrial portion of said prosthesis; and wherein said first section of said ventricular portion of said prosthesis is formed by diamond-shaped mesh portions similar to said diamond-shaped mesh portions forming said atrial and intermediate annular portions of said prosthesis, wherein said anchoring claws of said ventricular portion have said bases connected to said mesh portions that form said corners of said meshes situated upon said ventricular side of said prosthesis, and said anchoring claws protrude from said mesh portions toward said atrial side of said prosthesis.

* * * * *